United States Patent
Oku et al.

(10) Patent No.: US 7,358,338 B2
(45) Date of Patent: Apr. 15, 2008

(54) HEME PEPTIDE

(75) Inventors: Tadatake Oku, Tokyo (JP); Toshiyuki Nishio, Tokyo (JP); Ryu Kawachi, Tokyo (JP); Kohei Suruga, Tokyo (JP)

(73) Assignee: Nihon University (JP)

( * ) Notice: Subject to any disclaimer, the term of this patent is extended or adjusted under 35 U.S.C. 154(b) by 178 days.

(21) Appl. No.: 10/507,156

(22) PCT Filed: Feb. 28, 2003

(86) PCT No.: PCT/JP03/02394

§ 371 (c)(1),
(2), (4) Date: Jun. 7, 2006

(87) PCT Pub. No.: WO03/074564

PCT Pub. Date: Sep. 12, 2003

(65) Prior Publication Data

US 2006/0258563 A1    Nov. 16, 2006

(30) Foreign Application Priority Data

Mar. 4, 2002 (JP) .................... 2002-058086

(51) Int. Cl.
*C07K 14/805* (2006.01)
(52) U.S. Cl. .................................... 530/385
(58) Field of Classification Search ................ 530/385
See application file for complete search history.

(56) References Cited

U.S. PATENT DOCUMENTS 5,855,621 A    1/1999    Damhus et al.

OTHER PUBLICATIONS

Sugimura et al. 1981; Studies on algal cytochromes. III. Amino acid sequence of cytochrome c-553 from brown alga, *Petalonia fascia*. J. Biochem. 90(4): 1213-1219.*
Aron et al. 1986; Hemes and hemoproteins. 1: Preparation and analysis of the heme-containing octapeptide (microperoxidase-8) and identification of the monomeric form in aqueous solution. J. Inorg. Chem 27227-243.*

Samya Othman, et al.; "Resonance Raman investigation of lysine and N-acetylmethionine complexes of ferric and ferrous microperoxidase"; European Biophysics Journal: 1999; vol. 28(1); pp. 12-25.
Jinn-Shyan Wang, et al.; "Temperature-and-pH-dependent Changes in the Coordination Sphere of the Heme c Group in the Model Peroxidase Na-Acetyl Microperoxidase-8"; The Journal of Biological Chemistry; 1992; vol. 267(22); pp. 15310-15318.
Shyamalava Mazumdar, et al.; "Stability and Chracterization of Iron(III) and Iron(II) Heme Peptides Encapsulated in Aqueous Detergent Micelles: 1H NMR and UV-Vis Spectroscopic Studies"; Inorganic Chemistry; 1991; vol. 30(4); pp. 700-705.
Richard E. Dickerson, et al.; "Ferricytochrome c"; The Journal of Biological Chemistry; 1971; vol. 246(5); pp. 1511-1535.
Seiji Yamada, et al; "Structure of cytochrome c6 from the red alga *Porphyra yezoensis* at 1.57 A resolution"; Acta Crystallographica Section D; Biological Crysrallography; 2000; vol. D56(12); pp. 1577-1582.
"Issanka Chisso (NO) no Haem Tanpaku-shitsu ni yoru Hosoku"; Kagaku to Seibutsu; 1996; vol. 34(12): pp. 784-785.
Seiji Yamada, et al.; "Characterization and Amino Acid Sequences of Cytochromes c6 from Two Strains of the Green Alga *Chlorella vulgaris*"; Bioscience Biotechnology and Biochemistry; 2000; vol. 64(3); pp. 628-632.
Ricoux Remy et al., "Microperoxidase 8 catalyzed nitration of phenol by nitrogen dioxide radicals," Jul. 2001, European Journal of Biochemistry, vol. 268, nr. 13, pp. 3783-3788.
Ricoux Remy et al., "Formation of iron(II)-nitrosoalkane complexes: A new activity of microperoxidase 8," Nov. 2000, Biochemical and Biophysical Research Communications, vol. 278, nr. 1, pp. 217-223.

* cited by examiner

*Primary Examiner*—Karen Cochrane Carlson
(74) *Attorney, Agent, or Firm*—Dickstein Shapiro LLP

(57) ABSTRACT

A novel heme peptide and a method for producing the same are disclosed.

The invention provides a peptide with a potent NO-scavenging ability which can be used in capturing/quantifying NO and can be used as a diagnostic agent, prophylactic agent or therapeutic agent for diseases in which NO is involved, as a research reagent, as a reagent for measuring NO concentrations in the environment, and as a treating agent for removing NO in the environment.

4 Claims, No Drawings

HEME PEPTIDE

TECHNICAL FIELD

The present invention relates to novel heme peptides, particular, heme peptides having NO-scavenging ability, methods for producing the heme peptide, and NO scavengers and pharmaceutical compositions each comprising the heme peptide.

BACKGROUND ART

Recently, it has been reported that nitrogen monoxide (NO) is involved in lifestyle-related diseases such as diabetes, arteriosclerosis and cancer. More specifically, it has been reported that abnormality in NO production is involved in many physiological functions and diseases. For example, it is known that shortage of NO is responsible for hypertension, hyperlipemia, arteriosclerosis, heart failure, coronary spasm, etc., and that excess of NO is responsible for cerebral apoplexy, Huntington's disease, Parkinson's disease, etc.

On the other hand, NO is one of the environmental pollutant $NO_x$, and development NO-scavenging materials is important in measuring environmental pollution and in purifying polluted air, water or the like.

Thus, development of materials for quantifying or scavenging NO has been desired.

However, NO is a gas and unstable at normal temperatures. Therefore, it is difficult to handle or quantify NO. Further, no effective NO-scavenging materials have been known to date.

The present inventors have already found that cytochrome c has NO-scavenging ability (Chemistry and Organisms, 34 (12), 784-786 (1996)). Also, the inventors have isolated similar C-type cytochromes from various organisms such as red alga *Porphyra yezonesis*, green alga chlorella and photosynthetic bacteria, and confirmed NO-scavenging ability in them (Biosci. Biotechnol. Biochem., 64(3), 628-632, 2000; Jap. J. Pharmacol., 75 (Suppl. I), p. 113 (1997)). Further, the present inventors have determined the tertiary structure of red alga *Porphyra yezonesis*-derived cytochrome $c_6$ by three-dimensional structure analysis with x-ray (Acta Cryst., D56, 1577-1582 (2000)) and constructed an expression system for cytochrome $c_6$ in a recombinant *Escherichia coli*.

The present inventors have advanced further the research in materials having NO-scavenging ability, as a consequence they have found heme peptides having higher NO-scavenging ability than cytochrome c.

DISCLOSURE OF THE INVENTION

The present invention relates to a heme peptide represented by the following formula I.

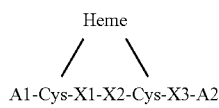

(I)

(where A1 is a hydrogen atom or a peptide chain consisting of 1 to 20, preferably 1 to 10, especially preferably 1 to 5, amino acid residues;

A2 is a hydroxyl group or a peptide chain consisting of 1 to 50, preferably 1 to 10, especially preferably 1 to 5, amino acid residues;

the heme is a heme nucleus represented by the following formula:

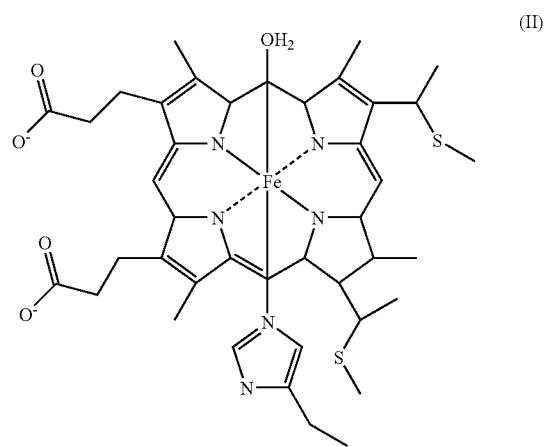

(II)

X1 and X2 each independently represent any amino acid residue; and

X3 is His, Lys or Arg.)(see SEQ ID NO: 11 for complete embodiment).

The heme nucleus described above is capable of linking to cysteine residues via the cysteinyl thioether bonds at positions 3 and 8.

(2) The heme peptide of (1) above, wherein X1 and X2 each independently represent an amino acid residue selected from the group consisting of Ala, Gln, Lys, Arg and Val (see SEQ ID NO: 12 for complete embodiment).

(3) The heme peptide of (1) above, wherein X1 is Ala; X2 is Gln or Ala; and X3 is His (see SEQ ID NO: 13 for complete embodiment).

(4) The heme peptide of (1) above, wherein
A1 is a hydrogen atom or a peptide chain having an amino acid sequence of Val Gln Lys;
A2 is a peptide chain having an amino acid sequence of Thr Val Glu Lys (SEQ ID NO: 14) or Thr Val Glu Lys Gly Gly Lys His Lys Thr Gly Pro Asn Leu (SEQ ID NO: 18);
X1 is Ala; X2 is Gln; and X3 is His (see SEQ ID NO: 5 for complete embodiment).

(5) The heme peptide of (1) above, wherein
A1 is a peptide chain having an amino acid sequence of Phe Ser Ala Asn (SEQ ID NO: 15);
A2 is a peptide chain having an amino acid sequence of Ala Gly Gly Asn Asn Ala (SEQ ID NO: 16);
X1 is Ala; X2 is Ala; and X3 is His (see SEQ ID NO: 3 for complete embodiment).

The present invention also relates to a method of producing the heme peptide of any one of (1) to (5) above, comprising digesting cytochrome c with a restriction enzyme, optionally conducting a salting out treatment, and purifying the resultant digest by gel filtration chromatography. Preferably, the restriction enzyme is selected from the group consisting of thermolysin, trypsin, chymotrypsin, *Achromobacter* protease I and *Staphylococcus aureus* V8 protease.

Further, the present invention relates to an NO-scavenger comprising the heme peptide of any one of (1) to (5) above.

The above-described peptide of the present invention is characterized by (a) comprising a peptide having an amino acid sequence spanning from Cys at position 14 to the amino acid residue at position 18 of cytochrome c in the shortest or this sequence in which the amino acid residues at positions 15, 16 and 18 are substituted; (b) its heme nucleus being bound to the Cys residues at positions 14 and 17 via the cysteinyl thioether bonds at positions 3 and 8; (c) the amino acid residue at potion 18 being His, Lys or Arg; (d) the amino acid residues at positions 15 and 16 being preferably Ala, Gln, Lys, Arg or Val; and (e) the N-terminal peptide chain of the Cys residue at position 14 and the C-terminal peptide chain of the Cys residue at position 17 each consisting of preferably 50 nucleotides or less, more preferably 10 nucleotides or less. As a result of intensive and extensive researches, the present inventors have found that such heme peptides have higher NO-scavenging ability than cytochrome c. It is believed that, probably, such higher ability is brought about because the number of solvent molecules per unit area increased as a result of decrease in the size of the peptide, and because the probability of collision with NO increased as a result of exposure of the heme nucleus to the solvent.

BEST MODE FOR CARRYING OUT THE INVENTION

As a specific example of A1, a peptide chain may be given which consists of 1 to 13 consecutive amino acid residues starting from position 13 and running to the N-terminal in a partial amino acid sequence spanning from position 1 to position 13 of SEQ ID NO: 1 (sequence for horse cardiac muscle cytochrome c) or SEQ ID NO: 2 (sequence for red alga *Porphyra yezonesis* cytochrome $c_6$) in the sequence listing, or in the partial amino acid sequence where one to several amino acids are substituted, deleted or added.

As a specific example of A2, a peptide chain may be given which consists of 1 to 50 consecutive amino acid residues starting from position 19 and running to the C-terminal in a partial amino acid sequence spanning from position 19 to position 70 of SEQ ID NO: 1 (sequence for horse cardiac muscle cytochrome c) or SEQ ID NO: 2 (sequence for red alga *Porphyra yezonesis* cytochrome $c_6$) in the sequence listing, or in the partial amino acid sequence where one to several amino acids are substituted, deleted or added.

In the present specification, the "NO-scavenger" may be for any purpose as long as it is capable of being used for capturing NO. Typically, the NO-scavenger is a diagnostic for use in measuring NO concentrations in the body (e.g. in blood), a prophylactic and/or therapeutic for diseases associated with excess of NO that captures NO in the body (e.g. in blood), a research reagent, a reagent for use in measuring NO concentrations in air, exhaust gas or water, or a treating agent for use in water treatment or exhaust gas treatment.

The heme peptide of the invention may also be prepared by introducing a vector comprising a DNA having a nucleotide sequence encoding the amino acid sequence of cytochrome c (or the DNA into which a site-specific mutation has been introduced) into a host cell, culturing the host cell, isolating the cytochrome c from the resultant culture, digesting the cytochrome c with a restriction enzyme, and purifying resultant digest by a method, such as chromatography. In this case, vectors which may be used for transformation include plasmids, phages, etc. that are conventionally used in the field of biotechnology. As a host cell, preferably a prokaryotic cell, more preferably a bacterium, especially *Escherichia coli* is used. The isolation of cytochrome c may be performed by, for example, harvesting cultured cells, disrupting the cells physically, and then extracting and purifying the cytochrome c. The harvesting of cultured cells may be performed by scraping off when the cells are cultured in a solid medium or by centrifugation when the cells are cultured in a liquid medium.

In the present invention, the term "cytochrome c" encompasses all the c-type cytochromes including cytochrome $c_1$, cytochrome $c_2$, cytochrome $c_6$, cytochrome c-551, and so on.

The "amino acid residues" constituting the peptide of the invention also include modified amino acid residues.

EXAMPLES

In the following Examples, reagents manufactured by Wako Purechemical Industries were used unless otherwise noted. Isoelectric point was analyzed by isoelectric focusing using Ampholine PAGplate gel (Pharmacia; for IEF; pH 3.5-9.5). Absorption maximum was determined with Hitachi U-3310 Spectrophotometer (Hitachi). Oxidation-reduction potential was determined with Hitachi U-3310 Spectrophotometer (Hitachi) and ORP electrode (Metrohm).

Example 1

Preparation of Heme Peptide (mp15)

A heme peptide having the following amino acid sequence was prepared.

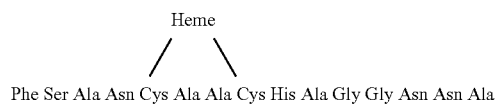

(The heme nucleus in formula II is bound to the cysteine residues at positions 5 and 8 of a peptide having the sequence as shown in SEQ ID NO: 3.)

One milligram of cytochrome $c_6$ purified from red alga *Porphyra yezonesis* was dissolved in 200 μl of 0.1 M Tris-HCl buffer (pH 7.8) (containing 2 mM calcium chloride). The resultant cytochrome $c_6$ solution was kept at 37° C. for 5 min. To this solution, 62.5 μl of 1 mg/ml thermolysin solution in 0.1 M Tris-HCl buffer was added. Further, 37.5 μl of the same buffer was added thereto. This reaction solution was kept at 37° C. for 4.5 hr. Then, the reaction solution was ice-cooled to terminate the reaction, and 700 μl of the same buffer was added thereto. The resultant reaction solution was purified by gel filtration column chromatography (Toyopearl HW-40F; 1.0×80 cm; Tosoh) to thereby obtain the above-described peptide. The resultant peptide was electrophoresed to thereby confirm that this peptide was a single substance. Further, the amino acid sequence of this peptide was analyzed with an amino acid sequencer to thereby confirm that this peptide had the above-described sequence.

The resultant peptide had the following physical properties: Isoelectric point: 4.15; Absorption maximum of oxidized type: 404, 526 nm; Absorption maximum of reduced type: 413.5, 549.5 nm; Oxidation-reduction potential: −82.2 mV; Molecular weight: 2200.

Example 2

Preparation of Heme Peptide (mp9)

A heme peptide having the following amino acid sequence was prepared.

Cys Ala Gln Cys His Thr Val Glu Lys (The heme nucleus in formula II is bound to the cysteine residues at positions 1 and 4 of a peptide having the sequence as shown in SEQ ID NO: 4.)

One milligram of horse cardiac muscle cytochrome c (Wako Purechemical Industries) was dissolved in 100 µl of 0.1 M Tris-HCl buffer (pH 8.0). The resultant cytochrome c solution was kept at 37° C. for 5 min. To this solution, 40 µl of 1 mg/ml trypsin solution in 0.1 M Tris-HCl buffer was added. Further, 60 µl of the same buffer was added thereto. This reaction solution was kept at 37° C. for 24 hr. Then, the reaction solution was ice-cooled to terminate the reaction. After addition of ammonium sulfate (78 mg), the precipitate was filtered out and the filtrate was purified by gel filtration column chromatography (Toyopearl HW-40F; 1.0×80 cm; Tosoh) to thereby obtain the above-described peptide. The resultant peptide was electrophoresed to thereby confirm that this peptide was a single substance. Further, the amino acid sequence of this peptide was analyzed with an amino acid sequencer to thereby confirm that this peptide had the above-described sequence.

The resultant peptide had the following physical properties: Isoelectric point: 4.95; Absorption maximum of oxidized type: 395, 619 nm; Absorption maximum of reduced type: 412, 520, 549 nm; Oxidation-reduction potential: −132 mV; Molecular weight: 1637.

Example 3

Preparation of Heme Peptide (mp22)

A heme peptide having the following amino acid sequence was prepared.

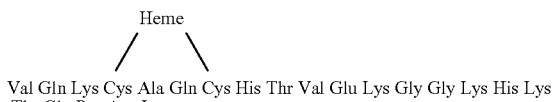

Val Gln Lys Cys Ala Gln Cys His Thr Val Glu Lys Gly Gly Lys His Lys Thr Gly Pro Asn Leu (The heme nucleus in formula II is bound to the cysteine residues at positions 4 and 7 of a peptide having the sequence as shown in SEQ ID NO: 5.)

One milligram of horse cardiac muscle cytochrome c (Wako Purechemical Industries) was dissolved in 100 µl of 0.1 M Tris-HCl buffer (pH 8.0). The resultant cytochrome c solution was kept at 37° C. for 5 min. To this solution, 40 µl of 1 mg/ml chymotrypsin solution in 0.1 M Tris-HCl buffer was added. Further, 60 µl of the same buffer was added thereto. This reaction solution was kept at 37° C. for 24 hr. Then, the reaction solution was ice-cooled to terminate the reaction. After addition of ammonium sulfate (78 mg), the precipitate was filtered out and the filtrate was purified by gel filtration column chromatography (Toyopearl HW-40F; 1.0×80 cm; Tosoh) to thereby obtain the above-described peptide. The resultant peptide was subjected to HPLC to thereby confirm that this peptide was a single substance. Further, the amino acid sequence of this peptide was analyzed with an amino acid sequencer to thereby confirm that this peptide had the above-described sequence.

The resultant peptide had the following physical properties: Isoelectric point: 6.02; Absorption maximum of oxidized type: 398, 620 nm; Absorption maximum of reduced type: 416, 520, 549 nm; Oxidation-reduction potential: −66.5 mV; Molecular weight: 3065.

Example 4

Preparation of Heme Peptide (mp65)

A heme peptide having the following amino acid sequence was prepared.

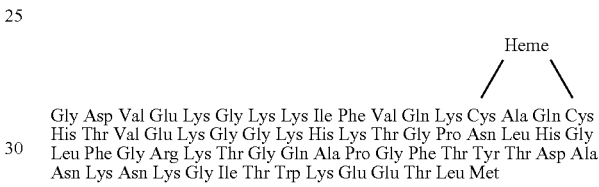

Gly Asp Val Glu Lys Gly Lys Lys Ile Phe Val Gln Lys Cys Ala Gln Cys
His Thr Val Glu Lys Gly Gly Lys His Lys Thr Gly Pro Asn Leu His Gly
Leu Phe Gly Arg Lys Thr Gly Gln Ala Pro Gly Phe Thr Tyr Thr Asp Ala
Asn Lys Asn Lys Gly Ile Thr Trp Lys Glu Glu Thr Leu Met (The heme nucleus in formula II is bound to the cysteine residues at positions 14 and 17 of a peptide having the sequence as shown in SEQ ID NO: 6.)

One milligram of horse cardiac muscle cytochrome c (Wako Purechemical Industries) was dissolved in 100 µl of 10 mg/ml cyanogens bromide (dissolved in 70% formic acid). Nitrogen gas was fed into the reaction tube. The resultant cytochrome c solution was kept at 20° C. for 24 hr. The reaction solution was water-cooled to terminate the reaction. Then, 400 µl of ultrapure water was added, and the resultant solution was purified by gel filtration column chromatography (Toyopearl HW-40F; 1.0×80 cm; Tosoh) to thereby obtain the above-described peptide. The resultant peptide was electrophoresed to thereby confirm that this peptide was a single substance. Further, the amino acid sequence of this peptide was analyzed with an amino acid sequencer to thereby confirm that this peptide had the above-described sequence.

The resultant peptide had the following physical properties: Isoelectric point: 9.52; Absorption maximum of oxidized type: 404, 535 nm; Absorption maximum of reduced type: 415, 520, 549 nm; Oxidation-reduction potential: −62.1 mV; Molecular weight: 8900.

Example 5

An NO-scavenging heme peptide represented by the following formula was prepared in the same manner as described in Example 3 except that *Achromobacter* protease I (lysyl endopeptidase) was used as a restriction enzyme instead of chymotrypsin.

(The heme nucleus in formula II is bound to the cysteine residues at positions 1 and 4 of a peptide having the sequence as shown in SEQ ID NO: 7.)

Example 6

An NO-scavenging heme peptide represented by the following formula was prepared in the same manner as described in Example 1 except that *Achromobacter* protease I (lysyl endopeptidase) was used as a restriction enzyme instead of thermolysin.

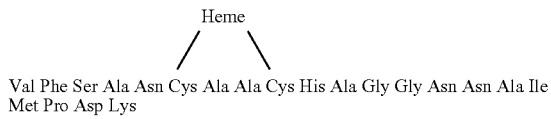

(The heme nucleus in formula II is bound to the cysteine residues at positions 6 and 9 of a peptide having the sequence as shown in SEQ ID NO: 8.)

Example 7

An NO-scavenging heme peptide represented by the following formula was prepared in the same manner as described in Example 3 except that *Staphylococcus aureus* V8 protease (endoprotenase Glu-C) was used as a restriction enzyme instead of chymotrypsin and that an ammonium buffer was used instead of the phosphate buffer.

(The heme nucleus in formula II is bound to the cysteine residues at positions 10 and 13 of a peptide having the sequence as shown in SEQ ID NO: 9.)

Example 8

An NO-scavenging heme peptide represented by the following formula was prepared in the same manner as described in Example 1 except that *Staphylococcus aureus* V8 protease (endoprotenase Glu-C) was used as a restriction enzyme instead of thermolysin and that an ammonium buffer was used instead of the phosphate buffer.

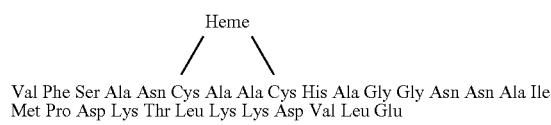

(The heme nucleus in formula II is bound to the cysteine residues at positions 6 and 9 of a peptide having the sequence as shown in SEQ ID NO: 10.)

Test Example 1

Measurement of NO-Scavenging Ability

To a 10 ml vial, 0.3 ml of 100 mM phosphate buffer (pH 7.0), 0.4 ml of 10 mM sodium nitrite, 0.5 ml of a solution of each of the above-described peptides, and 0.4 ml of 3 mM methyl viologen (Tokyo Kasei Kogyo) were added. Then, the vial was tightly sealed with a butyl rubber stopper and an aluminum seal. This vial was kept at 37° C. for 5 min while feeding argon gas thereinto. Then, 0.3 ml of 100 mM sodium dithionite (dissolved in 50 mM sodium hydrogencarbonate) was added thereto to start the reaction. A 0.2 ml sample was taken from the reaction solution at regular intervals and air-oxidized in a vortex mixer to thereby terminate the reaction.

The amount of the remaining nitrite was determined by the diazotization method. 0.02 ml of the reaction solution was taken, and 1.98 ml of ultrapure water was added thereto. Then, 1 ml of 1% sulfanilamide, 1 ml of 0.02% N-1-naphthyl ethylenediamine chloride and 1 ml of ultrapure water were added thereto. The resultant solution was left at room temperature for 20 min. Then, absorption of the produced azo dye was measured at 540 nm, followed by calculation of the amount of the remaining nitrite from a working curve prepared from a nitrous acid solution of a known concentration.

The measurement of absorption was performed with Shimadzu UV-1600 UV-Visible Spectrophotometer.

Analysis based on reaction kinetics was performed by determining specific activities against 2, 4, 6, 8 and 10 mM sodium nitrite and then calculating the reaction turnover number $k_{cat}(s^{-1})$ using a Lineweaver-Burk plot.

The rate constants of the peptides obtained in individual Examples are shown in the Table below.

For the purpose of comparison, the rate constants of horse cardiac muscle cytochrome c and red alga *Porphyra yezonesis* cytochrome $c_6$ are also shown.

TABLE 1

|  | Peptide | Rate Constant $k_{cat}$ (s$^{-1}$) |
|---|---|---|
| Example 1 | mp15 | 2.54 |
| Example 2 | mp9 | 1.66 |
| Example 3 | mp22 | 0.80 |
| Example 4 | mp65 | 0.12 |
| Comparative Example 1 | Horse cardiac muscle cytochrome c | 15.21 × 10$^{-3}$ |
| Comparative Example 2 | Red alga *Porphyra yezonesis* cytochrome $c_6$ | 0.05 |

From the above Table, it is clear that the heme peptide of the invention has a remarkably high NO-scavenging ability as compared to cytochrome c.

INDUSTRIAL APPLICABILITY

An NO-scavenger is provided which can be used as a reagent for quantifying NO in the body, as a pharmaceutical composition that controls NO in the body, as a reagent for measuring NO concentrations in environment, or as a purifying agent for polluted air and polluted waste water. Further, out of the heme peptides of the invention, those which are soluble in water are suitable for uses in liquid samples.

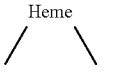

where the heme means the heme defined in formula I.

---

The invention claimed is:

1. A heme peptide selected from the group consisting of heme peptides represented by the following formulas:

(SEQ ID NO: 3)

Heme
/    \
Phe Ser Ala Asn Cys Ala Ala Cys His Ala Gly Gly Asn Asn Ala (SEQ ID NO: 8)

Heme
/    \
Val Phe Ser Ala Asn Cys Ala Ala Cys His Ala Gly Gly Asn Asn Ala Ile Met Pro Asp Lys and (SEQ ID NO: 10)

Heme
/    \
Val Phe Ser Ala Asn Cys Ala Ala Cys His Ala Gly Gly Asn Asn Ala Ile Met Pro Asp Lys Thr Leu Lys Lys Asp Val Leu Glu where the heme is a heme nucleus represented by the following formula:

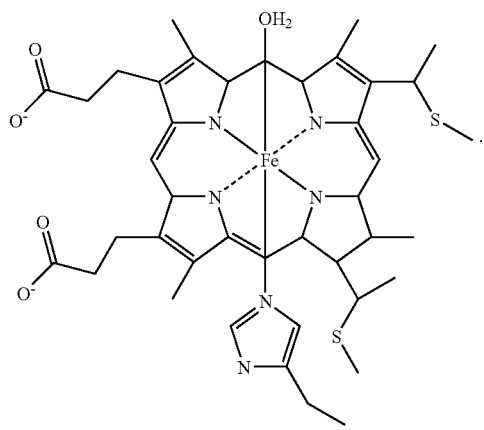

(II)

2. A method of producing the heme peptide according to claim 1, comprising digesting cytochrome c with a restriction enzyme and purifying the resultant digest by gel filtration chromatography.

3. The method according to claim 2, wherein the restriction enzyme is selected from the group consisting of thermolysin, trypsin, chymotrypsin, *Achromabacter* protease I and *Staphylococcus aureus* V8 protease.

4. An NO scavenger comprising the heme peptide according to claim 1.

* * * * *

SEQUENCE LISTING

<160> NUMBER OF SEQ ID NOS: 18

<210> SEQ ID NO 1
<211> LENGTH: 104
<212> TYPE: PRT
<213> ORGANISM: Equus caballus

<400> SEQUENCE: 1

```
Gly Asp Val Glu Lys Gly Lys Lys Ile Phe Val Gln Lys Cys Ala Gln
  1               5                  10                  15

Cys His Thr Val Glu Lys Gly Gly Lys His Lys Thr Gly Pro Asn Leu
             20                  25                  30

His Gly Leu Phe Gly Arg Lys Thr Gly Gln Ala Pro Gly Phe Thr Tyr
         35                  40                  45

Thr Asp Ala Asn Lys Asn Lys Gly Ile Thr Trp Lys Glu Glu Thr Leu
     50                  55                  60

Met Glu Tyr Leu Glu Asn Pro Lys Lys Tyr Ile Pro Gly Thr Lys Met
 65                  70                  75                  80

Ile Phe Ala Gly Ile Lys Lys Lys Thr Glu Arg Glu Asp Leu Ile Ala
                 85                  90                  95

Tyr Leu Lys Lys Ala Thr Asn Glu
            100
```

<210> SEQ ID NO 2
<211> LENGTH: 85
<212> TYPE: PRT
<213> ORGANISM: Porphyra yezoensis

<400> SEQUENCE: 2

```
Ala Asp Leu Asp Asn Gly Glu Lys Val Phe Ser Ala Asn Cys Ala Ala
  1               5                  10                  15

Cys His Ala Gly Gly Asn Asn Ala Ile Met Pro Asp Lys Thr Leu Lys
             20                  25                  30

Lys Asp Val Leu Glu Ala Asn Ser Met Asn Thr Ile Asp Ala Ile Thr
         35                  40                  45

Tyr Gln Val Gln Asn Gly Lys Asn Ala Met Pro Ala Phe Gly Gly Arg
     50                  55                  60

Leu Val Asp Glu Asp Ile Glu Asp Ala Ala Asn Tyr Val Leu Ser Gln
 65                  70                  75                  80
```

-continued

Ser Glu Lys Gly Trp
              85

<210> SEQ ID NO 3
<211> LENGTH: 15
<212> TYPE: PRT
<213> ORGANISM: Porphyra yezoensis

<400> SEQUENCE: 3

Phe Ser Ala Asn Cys Ala Ala Cys His Ala Gly Gly Asn Asn Ala
 1               5                  10                  15

<210> SEQ ID NO 4
<211> LENGTH: 9
<212> TYPE: PRT
<213> ORGANISM: Equus caballus

<400> SEQUENCE: 4

Cys Ala Gln Cys His Thr Val Glu Lys
 1               5

<210> SEQ ID NO 5
<211> LENGTH: 22
<212> TYPE: PRT
<213> ORGANISM: Equus caballus

<400> SEQUENCE: 5

Val Gln Lys Cys Ala Gln Cys His Thr Val Glu Lys Gly Gly Lys His
 1               5                  10                  15

Lys Thr Gly Pro Asn Leu
             20

<210> SEQ ID NO 6
<211> LENGTH: 65
<212> TYPE: PRT
<213> ORGANISM: Equus caballus

<400> SEQUENCE: 6

Gly Asp Val Glu Lys Gly Lys Lys Ile Phe Val Gln Lys Cys Ala Gln
 1               5                  10                  15

Cys His Thr Val Glu Lys Gly Gly Lys His Lys Thr Gly Pro Asn Leu
                 20                  25                  30

His Gly Leu Phe Gly Arg Lys Thr Gly Gln Ala Pro Gly Phe Thr Tyr
             35                  40                  45

Thr Asp Ala Asn Lys Asn Lys Gly Ile Thr Trp Lys Glu Glu Thr Leu
         50                  55                  60

Met
 65

<210> SEQ ID NO 7
<211> LENGTH: 9
<212> TYPE: PRT
<213> ORGANISM: Equus caballus

<400> SEQUENCE: 7

Cys Ala Gln Cys His Thr Val Glu Lys
 1               5

```
<210> SEQ ID NO 8
<211> LENGTH: 21
<212> TYPE: PRT
<213> ORGANISM: Porphyra yezoensis

<400> SEQUENCE: 8

Val Phe Ser Ala Asn Cys Ala Ala Cys His Ala Gly Gly Asn Asn Ala
 1               5                  10                  15

Ile Met Pro Asp Lys
            20

<210> SEQ ID NO 9
<211> LENGTH: 17
<212> TYPE: PRT
<213> ORGANISM: Equus caballus

<400> SEQUENCE: 9

Lys Gly Lys Lys Ile Phe Val Gln Lys Cys Ala Gln Cys His Thr Val
 1               5                  10                  15

Glu

<210> SEQ ID NO 10
<211> LENGTH: 29
<212> TYPE: PRT
<213> ORGANISM: Porphyra yezoensis

<400> SEQUENCE: 10

Val Phe Ser Ala Asn Cys Ala Ala Cys His Ala Gly Gly Asn Asn Ala
 1               5                  10                  15

Ile Met Pro Asp Lys Thr Leu Lys Asp Val Leu Glu
            20                  25

<210> SEQ ID NO 11
<211> LENGTH: 75
<212> TYPE: PRT
<213> ORGANISM: Artificial Sequence
<220> FEATURE:
<223> OTHER INFORMATION: Description of Artificial Sequence: Synthetic
      Formula Peptide
<220> FEATURE:
<221> NAME/KEY: MISC_FEATURE
<222> LOCATION: (1)..(20)
<223> OTHER INFORMATION: this region may encompass 1-20 variable amino
      acids or not be present; see specification as filed for detailed
      description of preferred embodiments
<220> FEATURE:
<221> NAME/KEY: MISC_FEATURE
<222> LOCATION: (22)..(23)
<223> OTHER INFORMATION: any amino acid
<220> FEATURE:
<221> NAME/KEY: MISC_FEATURE
<222> LOCATION: (25)
<223> OTHER INFORMATION: His, Lys or Arg
<220> FEATURE:
<221> NAME/KEY: MISC_FEATURE
<222> LOCATION: (26)..(75)
<223> OTHER INFORMATION: this region may encompass 1-50 variable amino
      acids or not be present; see specification as filed for detailed
      description of preferred embodiments

<400> SEQUENCE: 11

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Cys Xaa Xaa Cys Xaa Xaa Xaa Xaa Xaa Xaa Xaa Xaa
            20                  25                  30
```

-continued

```
Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa
 65                  70                  75

<210> SEQ ID NO 12
<211> LENGTH: 75
<212> TYPE: PRT
<213> ORGANISM: Artificial Sequence
<220> FEATURE:
<223> OTHER INFORMATION: Description of Artificial Sequence: Synthetic
      Formula Peptide
<220> FEATURE:
<221> NAME/KEY: MISC_FEATURE
<222> LOCATION: (1)..(20)
<223> OTHER INFORMATION: this region may encompass 1-20 variable amino
      acids or not be present; see specification as filed for detailed
      description of preferred embodiments
<220> FEATURE:
<221> NAME/KEY: MISC_FEATURE
<222> LOCATION: (22)..(23)
<223> OTHER INFORMATION: Ala, Gln, Lys, Arg or Val
<220> FEATURE:
<221> NAME/KEY: MISC_FEATURE
<222> LOCATION: (25)
<223> OTHER INFORMATION: His, Lys or Arg
<220> FEATURE:
<221> NAME/KEY: MISC_FEATURE
<222> LOCATION: (26)..(75)
<223> OTHER INFORMATION: this region may encompass 1-50 variable amino
      acids or not be present; see specification as filed for detailed
      description of preferred embodiments

<400> SEQUENCE: 12

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Cys Xaa Xaa Cys Xaa Xaa Xaa Xaa Xaa Xaa Xaa
         20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa
 65                  70                  75

<210> SEQ ID NO 13
<211> LENGTH: 75
<212> TYPE: PRT
<213> ORGANISM: Artificial Sequence
<220> FEATURE:
<223> OTHER INFORMATION: Description of Artificial Sequence: Synthetic
      Formula Peptide
<220> FEATURE:
<221> NAME/KEY: MISC_FEATURE
<222> LOCATION: (1)..(20)
<223> OTHER INFORMATION: this region may encompass 1-20 variable amino
      acids or not be present; see specification as filed for detailed
      description of preferred embodiments
<220> FEATURE:
<221> NAME/KEY: MISC_FEATURE
<222> LOCATION: (23)
<223> OTHER INFORMATION: Gln or Ala
<220> FEATURE:
<221> NAME/KEY: MISC_FEATURE
<222> LOCATION: (26)..(75)
```

```
<223> OTHER INFORMATION: this region may encompass 1-50 variable amino
      acids or not be present; see specification as filed for detailed
      description of preferred embodiments

<400> SEQUENCE: 13

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Cys Ala Xaa Cys His Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa
 65                  70                  75

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Val Glu Lys
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Ser Ala Asn
 1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Gly Gly Asn Asn Ala
 1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Glu Lys Cys Ala Glu Cys His Thr Val Glu
 1               5                  10

<210> SEQ ID NO 18
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Val Glu Lys Gly Gly Lys His Lys Thr Gly Pro Asn Leu
 1               5                  10
```